United States Patent
Kim

(10) Patent No.: US 9,179,725 B2
(45) Date of Patent: Nov. 10, 2015

(54) ROLLABLE SUN CAP

(76) Inventor: Bok Gyu Kim, Busan (KR)

( * ) Notice: Subject to any disclaimer, the term of this patent is extended or adjusted under 35 U.S.C. 154(b) by 211 days.

(21) Appl. No.: 13/882,889

(22) PCT Filed: Oct. 28, 2011

(86) PCT No.: PCT/KR2011/008128
§ 371 (c)(1),
(2), (4) Date: May 1, 2013

(87) PCT Pub. No.: WO2012/060582
PCT Pub. Date: May 10, 2012

(65) Prior Publication Data
US 2013/0212778 A1      Aug. 22, 2013

(30) Foreign Application Priority Data
Nov. 2, 2010   (KR) .................. 10-2010-0108335

(51) Int. Cl.
*A42B 1/20* (2006.01)
*A42B 1/06* (2006.01)
*A61F 9/04* (2006.01)

(52) U.S. Cl.
CPC .............. *A42B 1/201* (2013.01); *A42B 1/062* (2013.01); *A61F 9/045* (2013.01)

(58) Field of Classification Search
CPC ............ A42B 1/02; A42B 1/063; A42C 1/06; A42C 5/00
See application file for complete search history.

(56) References Cited

U.S. PATENT DOCUMENTS

| 236,316 | A | * | 1/1881 | Faught | 2/175.5 |
|---|---|---|---|---|---|
| 1,005,682 | A | * | 10/1911 | Bendel | 2/175.2 |
| 1,096,827 | A | * | 5/1914 | Comey | 2/175.5 |
| 5,572,745 | A | * | 11/1996 | Mainus | 2/171.2 |
| 5,857,219 | A | | 1/1999 | Edmark | |
| 5,950,241 | A | | 9/1999 | Gomez | |
| 6,311,331 | B1 | * | 11/2001 | Park | 2/195.1 |
| 6,408,443 | B1 | * | 6/2002 | Park | 2/195.1 |
| 6,964,064 | B1 | * | 11/2005 | Yan | 2/175.2 |
| 2003/0074715 | A1 | * | 4/2003 | Yl Park | 2/175.1 |
| 2004/0123376 | A1 | * | 7/2004 | Wang | 2/171.1 |
| 2004/0194192 | A1 | * | 10/2004 | Cho | 2/195.1 |

FOREIGN PATENT DOCUMENTS

| JP | 2003013320 | 1/2003 |
|---|---|---|
| JP | 2010116658 | 5/2010 |
| KR | 20-0168851 | 2/2000 |

* cited by examiner

*Primary Examiner* — Shaun R Hurley
*Assistant Examiner* — Andrew W Sutton
(74) *Attorney, Agent, or Firm* — IPLA P.A.; James E. Bame

(57) ABSTRACT

A rollable sun cap having a visor (10) having a body (10*a*) having upper and lower outer skins (13 and 14) adapted to cover the upper and lower portions of a core material thereof and a finishing edge (16) coupled by sewing to the outer circumference of the body (10*a*) and a band type hair portion (20) provided on the inner circumference of the visor (10) and having male and female magic tapes (24 and 25) detachably mounted on both ends thereof, the rollable sun cap including: adhesive surfaces (13*a*) formed on the inner surfaces of the upper and lower outer skins (13 and 14) facing the core material; and band type core materials (11) provided as the core material of the body (10*a*) of the visor (10).

7 Claims, 5 Drawing Sheets

ROLLABLE SUN CAP

BACKGROUND OF THE INVENTION

1. Field of the Invention

The present invention relates to a rollable sun cap, and more particularly, to a rollable sun cap that is provided with a body of a visor rollably formed in such a manner where band type core materials are spaced apart from each other by a given distance between upper and lower outer skins, and an elastic support wire mounted on the outer circumference of the body of the visor to maintain the given distance between the neighboring band type core materials, without having any distortion on the given distance, and to keep the shape of the visor when spread out, so that the sun cap can be rolled up for convenient storage when not in use and the visor can be spread out tightly, without any distorted portions, when the rolled up sun cap is spread out to be put on a wearer's head.

2. Background of the Related Art

As one of the prior art documents, there is disclosed Korean Patent No. 10-069190 (entitled "cap with partially incised brim"), wherein the cap includes a crown as a body of the cap made of at least one or more panels and a brim attached to the front lower end portion of the crown and having a core made of any one of soft, medium, and hard materials and upper and lower fabrics adapted to cover the core, the core having at least one or more partially incised portions formed thereon.

In the conventional practice, the core 2 of the brim has a plurality of incised lines 3 spaced apart from each other by a given distance thereon, thereby allowing the cap to be rolled up.

By the way, as shown in FIG. 11, both ends of the incised lines 3 are connected to the brim body, without any separation, thereby forming connection portions 4.

The core 2 of the brim is formed of a generally thin synthetic resin plate having a thickness of about 1 to 2 mm, and accordingly, even though the incised lines are not formed on the thin synthetic resin plate, the brim can be rolled up by means of the characteristics of the soft material. Further, at this time, the incised lines 3 are spaced apart from each other by the given distance on the core 2 made of the thin synthetic resin plate, so that the brim can be rolled up more gently.

By the way, both ends of the incised lines 3 are not incised up to the outside, but are connected integrally to the brim by means of the connection portions 4, so that when the core 2 is rolled up to a small-sized cylindrical shape or when the connection portions 4 are drastically bent, the connection portions 4 of the core 2 made of the thin synthetic resin plate may be cut or distorted.

If the cap having the core 2 on which the connection portions 4 are cut or bent is put on a wearer's head, the outer circumferential portion of the brim looks bent by the cut portion 5 or the bent portion 6 of each connection portion 4, thereby giving bad influences on the outer appearance of the cap.

On the other hand, it will be noted that the brim explained in the conventional practice is the same as a visor as will be explained in the present invention and the incised lines in the conventional practice are similar to a plurality of band type core materials spaced apart from each other by a given distance as will be discussed in the present invention.

SUMMARY OF THE INVENTION

Accordingly, the present invention has been made in view of the above-mentioned problems occurring in the prior art, and it is an object of the present invention to provide a rollable sun cap that is provided with a body of a visor rollably formed in such a manner where band type core materials are spaced apart from each other by a given distance between upper and lower outer skins, and an elastic support wire mounted on the outer circumference of the body of the visor to maintain the given distance between the neighboring band type core materials, without having any distortion on the given distance, and to keep the shape of the visor when spread out, so that the sun cap can be rolled up for convenient storage when not in use, and the visor can be spread out tightly, without any distorted portions, when the rolled up sun cap is spread out to be put on a wearer's head.

To accomplish the above object, according to the present invention, there is provided a rollable sun cap having a visor having a body having upper and lower outer skins adapted to cover the upper and lower portions of a core material thereof and a finishing edge coupled by sewing to the outer circumference of the body and a band type hair portion provided on the inner circumference of the visor and having male and female Magic Tapes®, hook and loop fabric detachably mounted on both ends thereof, the rollable sun cap including: adhesive surfaces formed on the inner surfaces of the upper and lower outer skins facing the core material; a plurality of band type core materials provided as the core material of the body of the visor in such a manner as to be spaced apart from each other by a given distance and attached to the adhesive surfaces formed on the upper and lower outer skins; and an elastic support wire mounted along the finishing edge in such a manner as to maintain the given distance between the neighboring band type core materials and to support the outer circumference of the visor.

BRIEF DESCRIPTION OF THE DRAWINGS

The above and other objects, features and advantages of the present invention will be apparent from the following detailed description of the preferred embodiments of the invention in conjunction with the accompanying drawings, in which.

DETAILED DESCRIPTION OF THE PREFERRED EMBODIMENT

Hereinafter, an explanation on a rollable sun cap according to the present invention will be in detail given with reference to the attached drawing.

Figure 1:
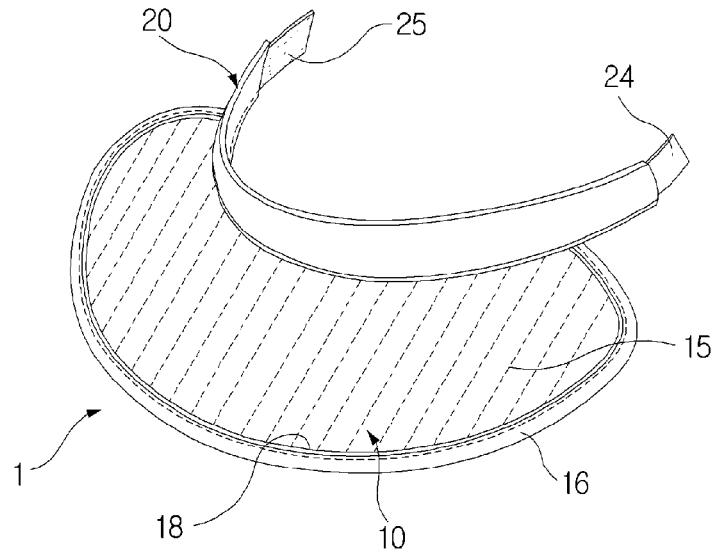
FIG. 1 is a perspective view showing a rollable sun cap according to a first embodiment of the present invention.
Figure 2:
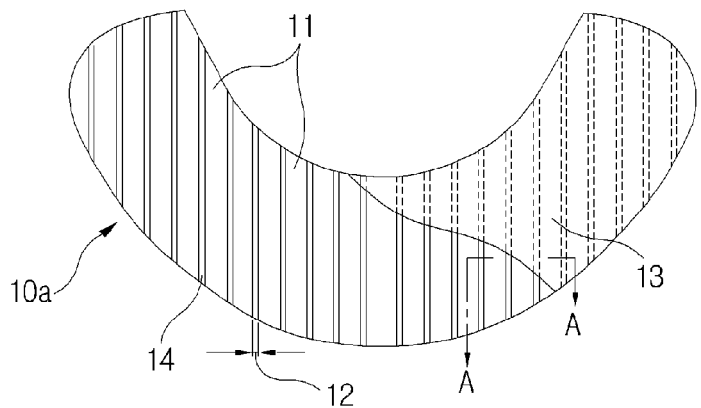
FIG. 2 is a plan view showing a body of a visor of the rollable sun cap according to the first embodiment of the present invention.
Figure 3:
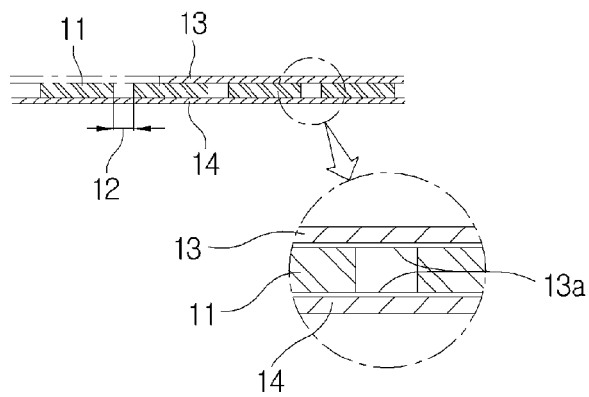
FIG. 3 is an enlarged sectional view showing the line A-A of FIG. 2.

As shown in FIGS. 1 to 3, a rollable sun cap 1 according to the first embodiment of the present invention includes: a visor 10 having a body 10a covered by upper and lower outer skins 13 and 14 disposed on the top and underside of a core material and a finishing edge 16 coupled by sewing to the front outer circumference of the body 10a; and a hair band portion 20 disposed on the rear inner circumference of the visor 10 and having male and female hook and loop fabric 24 and 25 detachably mounted on both ends thereof.

Further, each of the upper and lower outer skins 13 and 14 facing the core material has an adhesive surface 13a formed on the inner surface thereof, and the core material is formed of a plurality of band type core materials 11 spaced apart from each other by a given distance 12 in such a manner as to be attached between the upper and lower outer skins 13 and 14 by means of the adhesive surfaces 13a formed on the inner surfaces of the upper and lower outer skins 13 and 14.

At this time, the given distance 12 formed between the neighboring band type core materials 11 is formed in left and right directions, and the adhesive surfaces 13a formed on the inner surfaces of the upper and lower outer skins 13 and 14 are formed to face each other in such a manner as to be attached to the top and underside surfaces of the band type core materials 11. Further, adhesive surfaces 13a formed on the inner surfaces of the upper and lower outer skins 13 and 14 are of course attached to each other in each given distance 12.

Figure 4:
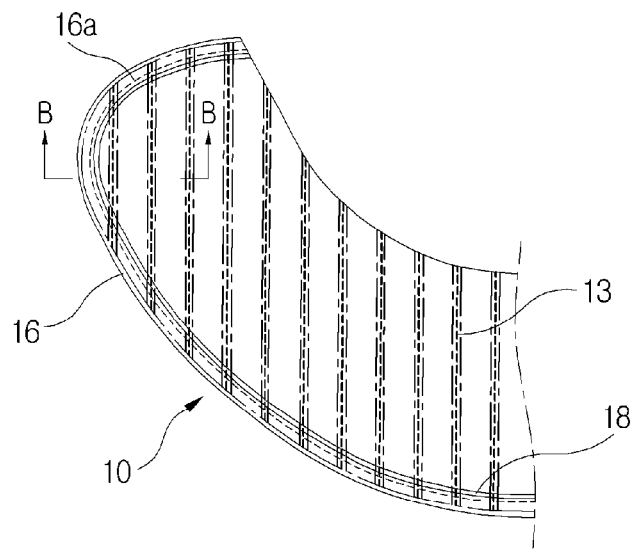
FIG. 4 is a plan view showing a portion of the body of the visor of the rollable sun cap according to the first embodiment of the present invention.
Figure 5:
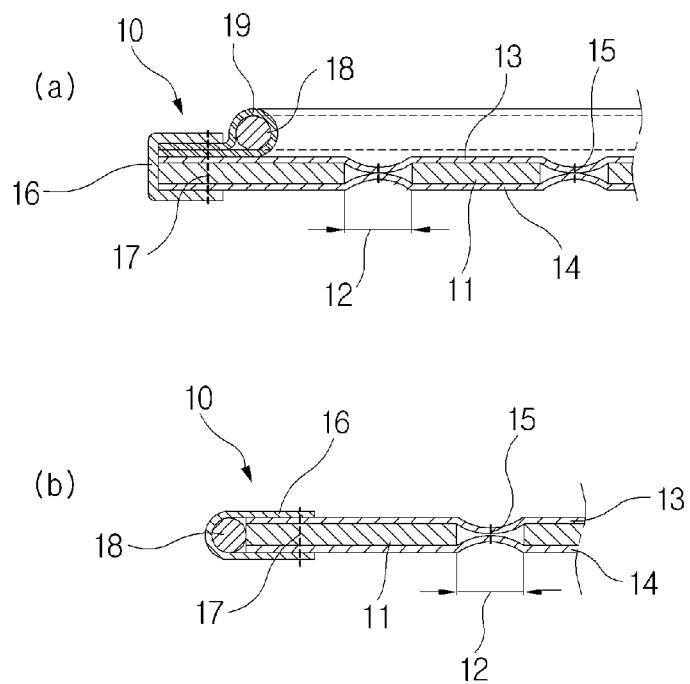
FIGS. 5a and 5b are enlarged sectional views showing the line B-B of FIG. 4, wherein the installation positions of an elastic support wire are different from each other.

As shown in FIGS. 4 and 5, the upper and lower outer skins 13 and 14, which are attached to each other in each given distance 12, are coupled to each other by means of sewing to form a plurality of sewn lines 15. The plurality of sewn lines 15 is formed forwardly and backwardly in the longitudinal direction in the space between the neighboring band type core materials 11, thereby preventing the upper and lower outer skins 13 and 14 from being open due to the weakness of the adhesion force of the adhesive surfaces 13a.

Further, the finishing edge 16 has an elastic support wire 18 adapted to maintain the given distance 12 between the neighboring band type core materials 11 and to support the outer circumference of the visor 10, and as shown in FIG. 5a, the elastic support wire 18 is surrounded with a wire cover 19, and then, in the state where the end portions of the open side of the wire cover 19 are inserted into the interior of the finishing edge 16, the finishing edge 16 and the wire cover 19 are sewn to each other in such a manner as to place the elastic support wire 18 on the top side of the outer circumference of the visor 10. Alternatively, as shown in FIG. 5b, in the state where the elastic support wire 18 is surrounded with the finishing edge 16, the top and underside portions of the finishing edge 16 are coupled by sewing to the outer circumference of the visor 10.

Each band type core material 11 is formed of a thin synthetic resin plate having a given elastic force, and the elastic support wire 18 is formed of a synthetic resin wire having a given elastic force, which is desirably formed of a fishing string having a diameter of about 2 mm.

Figure 6:
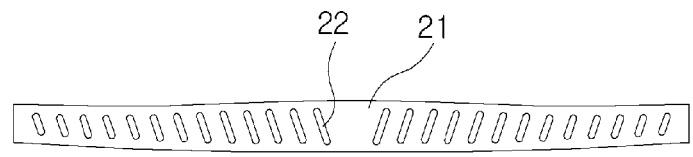
FIG. 6 is a front view showing a hair band core material of the rollable sun cap according to the first embodiment of the present invention.
Figure 7:
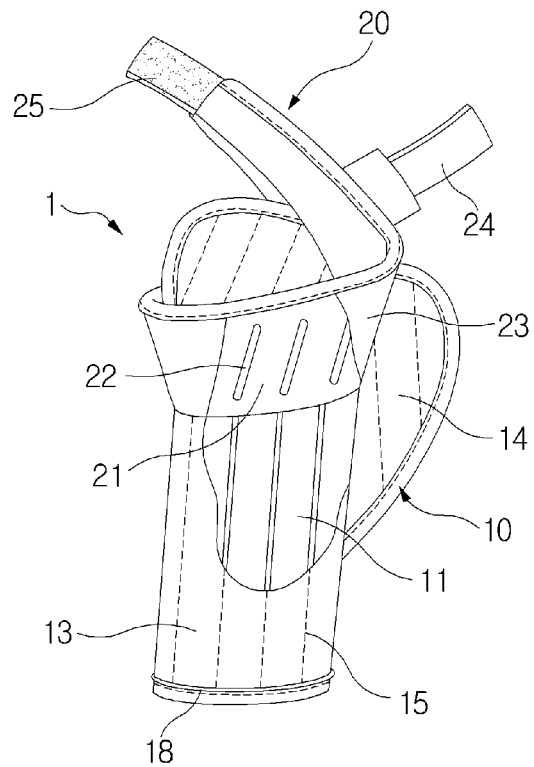
FIG. 7 is a perspective view showing a rolling process of the rollable sun cap according to the first embodiment of the present invention.

The hair band portion 20 includes an outer skin 23 and a hair band core material 21 inserted into the outer skin 23, and desirably, the hair band core material 21 is formed of a thin synthetic resin plate. As shown in FIGS. 6 and 7, the hair band core material 21 has incised portions 22 formed thereon in such a manner as to linearly correspond to the respective given distances 12, and thus, if it is desired to roll the sun cap 1 up, the visor 10 and the hair band portion 20 are gently rolled up together.

Further, even though not shown, the hair band core material 21 may be formed of an elastic material allowing the hair band portion 20 to be rolled up inwardly, so that the hair band portion 20 can be rolled up by means of the elastic force of the hair band core material 21 when the sun cap 1 is taken off.

Instead of the male and female hook and loop fabric 24 and 25 detachably mounted on both ends of the hair band portion 20, further, male and female buttons may be mounted as coupling means.

Figure 8:
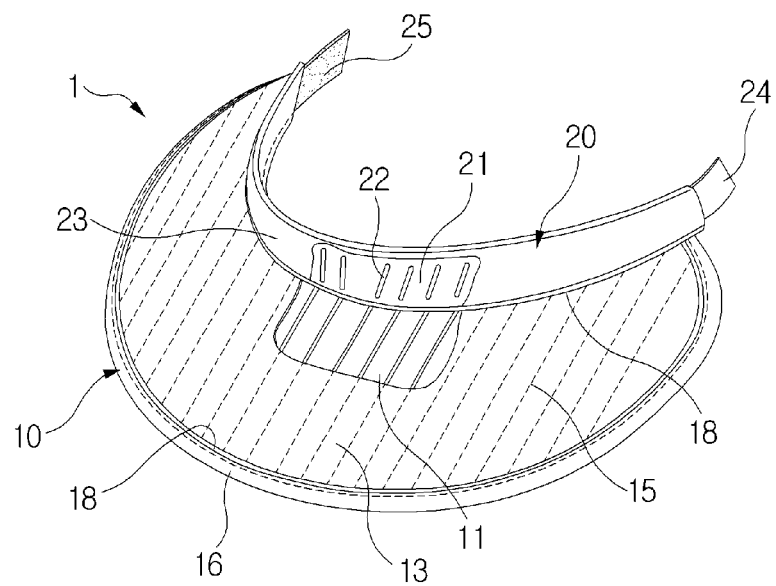
FIG. 8 is a perspective view showing a rollable sun cap according to a second embodiment of the present invention.

FIG. 8 is a perspective view showing a rollable sun cap according to a second embodiment of the present invention. According to the second embodiment of the present invention, another elastic support wire 18 is mounted on the connected portion between the visor 10 and the hair band portion 20 of the sun cap 1, that is, along the whole circumference of the visor 10, thereby allowing the visor 10 to be stretched out tightly.

Figure 9:
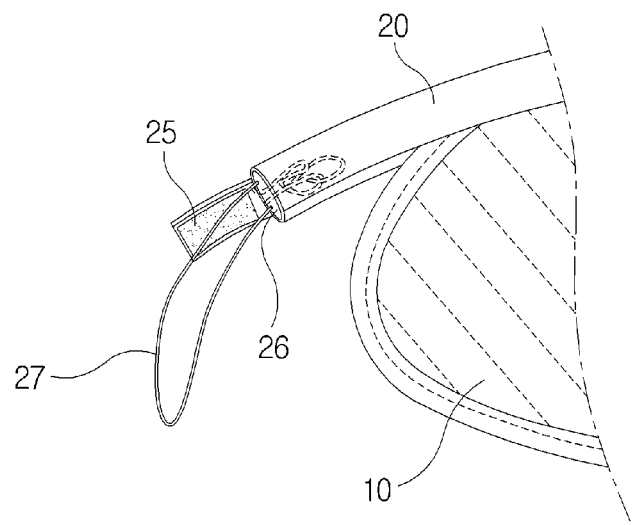
FIG. 9 is a perspective view showing the state where a binding string is mounted on the rollable sun cap according to the second embodiment of the present invention.
Figure 10:
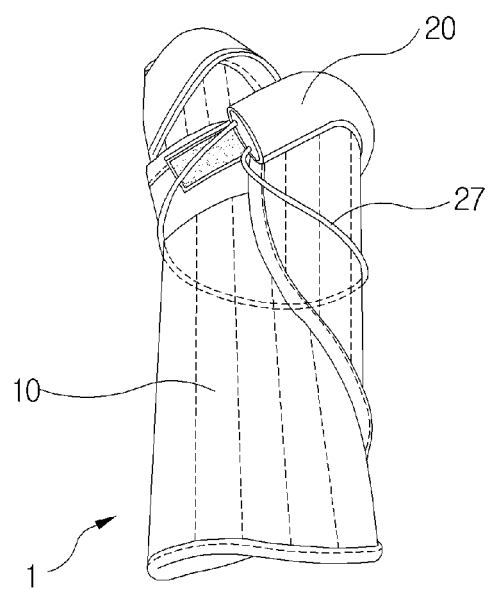
FIG. 10 is a perspective view showing the state where the binding string is wound on the rollable sun cap according to the second embodiment of the present invention.
Figure 11:
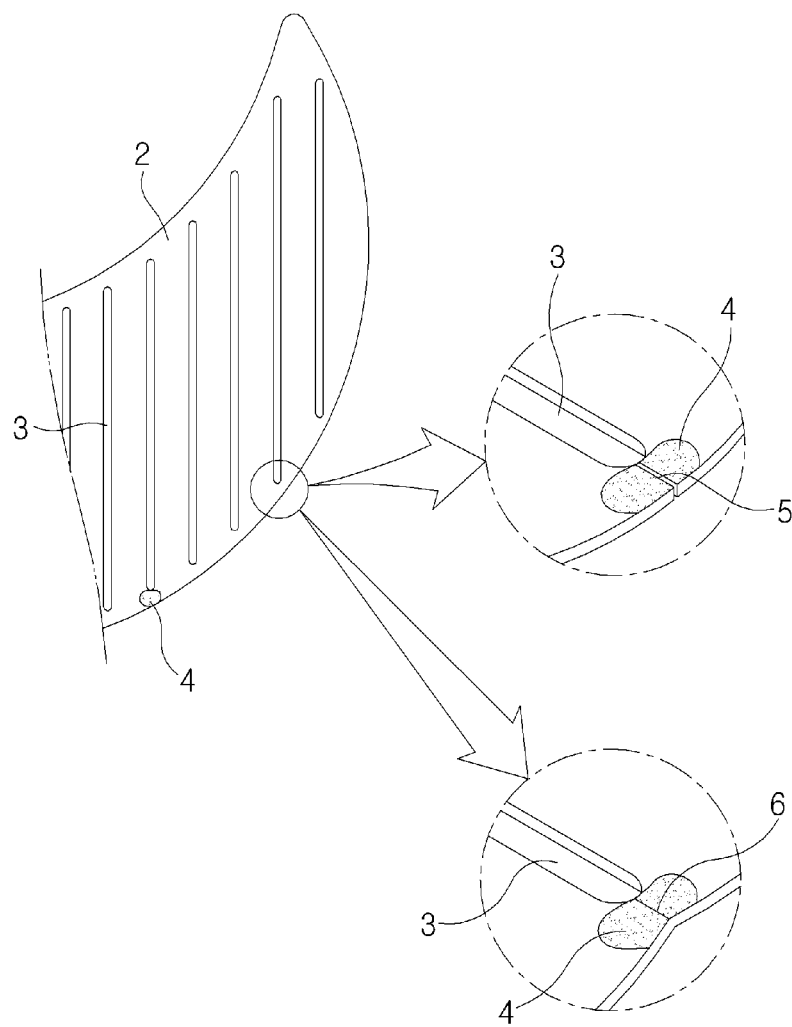
FIG. 11 is an enlarged plan view showing a conventional rollable sun cap.

FIGS. 9 and 10 show the states where the sun cap 1 is rolled up to a cylindrical shape, without any unrolling. To do this, a pocket 26 is formed on one side end of the hair band portion 20, and a binding string 27 is mounted on the open portion of the pocket 26.

A reference numeral 17 not explained yet denotes a sewing line for the finishing edge 16 coupled to the outer circumference of the visor body 10a.

Now, an operating relation of the rollable sun cap 1 according to the preferred embodiments of the present invention will be explained with reference to FIGS. 1 to 10.

The sun cap 1 as shown in FIG. 1 is in a free state where it is placed on a floor, without any wearing, and as shown in FIG. 2, the band type core materials 11 are spaced apart from each other by the given distance 12 between the upper and lower outer skins 13 and 14 of the body 10a of the visor 10 generally formed of a fabric, so that they may be contracted inwardly by the widths of the respective given distances 12 within the respective distances 12.

However, as shown in FIGS. 1 and 4 to 5b, the elastic support wire 18 like a fishing string having a diameter of about 2 mm is provided so that the visor 10 can be generally bent roundly like a thick fishing string bent roundly, without having any inward contraction of the band type core materials 11.

Further, the band type core materials 11 are spaced apart from each other by the given distance 12 between the upper and lower outer skins 13 and 14 of the body 10a of the visor 10, so that when the visor 10 is rolled up to a cylindrical shape, the rolling operation is gently performed.

The band type core materials 11, which are spaced apart from each other by the given distance 12 between the upper and lower outer skins 13 and 14 on which the adhesive surfaces 13a are formed, are attached to the adhesive surfaces 13a, so that if it is desired to make the body 10a of the visor 10 as shown in FIG. 2, the band type core materials 11 can be attached to the adhesive surfaces 13a, while being spaced apart from each other by the given distance 12, and they can be also integrally formed with the upper and lower outer skins 13 and 14 by means of the adhesive surfaces 13a, without any separation from the upper and lower outer skins 13 and 14.

That is, the adhesive surfaces 13a of the upper and lower outer skins 13 and 14 are attached to the top and underside surfaces of the band type core materials 11, and the adhesive surface 13a of the upper outer skin 13 is facedly attached to the adhesive surface 13a of the lower outer skin 14 in the given distance 12 between the neighboring band type core materials 11, so that the body 10a of the visor 10 is formed by integrally locating the band type core materials 11 between the upper and lower outer skins 13 and 14 in such a manner as to be spaced apart from each other by the given distance 12.

By the way, as shown in FIGS. 1 and 4 to 5b, the plurality of sewn lines 15 is formed in the given distances 12 between the neighboring band type core materials 11 to couple the upper and lower outer skins 13 and 14 attached to each other by means of the adhesive surfaces 13a to each other, which is prepared for the weakness of the adhesion force of the adhesive surfaces 13a because of the usage for a long period of time, thereby previously preventing the upper and lower outer skins 13 and 14 from being separated from each other.

The hair band core material 21 mounted at the inside of the hair band outer skin 23 of the hair band portion 20 has the plurality of incised portions 22 spaced apart from each other, so that when the sun cap 1 is rolled up, as shown in FIG. 7, the hair band portion 20 can be rolled up gently by means of the formation of the plurality of incised portions 22.

At this time, the given distances 12 formed on the visors 10 and the plurality of incised portions 22 formed on the hair band core material 21 are formed linearly to correspond to each other, so that the sun cap 1 is rolled up more gently.

If it is desired to reduce the volume of the sun cap 1 while the sun cap 1 is being carried or kept, the sun cap 1 according to the present invention can be conveniently rolled up. After rolled up, as shown in FIGS. 9 and 10, the binding string 27 inserted into the pocket 26 formed on one side of the hair band portion 20 is drawn to the outside and wound onto the sun cap 1 rolled up to the cylindrical shape, thereby completely preventing the sun cap 1 from being unrolled.

If there is no the binding string 27, further, the sun cap 1 may be kept into a bag having a cylindrical space formed at the inside thereof. On the other hand, the binding string 27 is not mounted just on the hair band portion 20, but it may be mounted on any positions of the inner side of the sun cap 1 unless the sun cap 1 is unrolled.

So as to use the sun cap 1 kept at the state of being rolled up, if the sun cap 1 is released from the binding string 27 or the bag, the elastic support wire 18 mounted on the visor 10 is stretched out tightly by means of its elastic force, without having any bending or having any wrinkling on the visor 10.

After the sun cap 1 is unrolled, if the binding string 27 is inserted into the pocket 26 formed on one side of the inside of the hair band portion 20, like one dot one dash line as shown in FIG. 9, it is not exposed to the outside, thereby preventing the outer appearance of the sun cap 1 from looking bad.

After the sun cap 1 has been unrolled, it is put on a wearer's head, and since the visor 10 has the distances 12 formed by the band type core materials 11 in such a manner as to place the upper and lower outer skins 13 and 14 thereon, the air ventilation is carried out through the distances 12 to allow wind to blow toward the wearer's face, while the sun light is being blocked.

As described above, the rollable sun cap according to the present invention is provided with the body of the visor rollably formed in such a manner where the band type core materials are spaced apart from each other by the given distance between the upper and lower outer skins, and the elastic support wire mounted on the outer circumference of the body of the visor, so that the sun cap can be rolled up well, thereby greatly reducing the volume thereof when carried or kept, and the visor can be spread out tightly, without any distorted portions, when the rolled up sun cap is spread out to be put on a wearer's head, thereby giving no bad influence on the outer appearance of the sun cap.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. A rollable sun cap comprising:
    a visor (10) having a body (10a) having upper and lower outer skins (13 and 14) adapted to cover the upper and lower portions of a core material thereof;
    a finishing edge (16) coupled by sewing to the outer circumference of the body (10a);
    a band type hair portion (20) provided on the inner circumference of the visor (10);
    male and female hook and loop fabric (24 and 25) detachably mounted on both ends thereof;
    adhesive surfaces (13a) formed on the inner surfaces of the upper and lower outer skins (13 and 14) facing the core material; and
    a plurality of band type core materials (11) provided as the core material of the body (10a) of the visor (10) in such a manner as to be spaced apart from each other by a given distance (12) and attached to the adhesive surfaces (13a) formed on the upper and lower outer skins (13 and 14).

2. The rollable sun cap according to claim 1, wherein the visor (10) further comprises a plurality of sewn lines (15) formed by sewing to couple the upper and lower outer skins (13 and 14) attached correspondingly to each other in the given distance (12) and an elastic support wire (18) mounted along the finishing edge (16) in such a manner as to maintain the given distance (12) between the neighboring band type core materials (11) and to support the outer circumference of the visor (10).

3. The rollable sun cap according to claim 1, wherein the hair band portion (20) comprises an outer skin (23) and a hair band core material (21) inserted into the outer skin (23).

4. The rollable sun cap according to claim 3, wherein the hair band core material (21) comprises incised portions (22) formed thereon in such a manner as to linearly correspond to the respective distances (12).

5. The rollable sun cap according to claim 3, wherein the hair band core material (21) is formed of an elastic material capable of inwardly rolling up the hair band portion (20).

6. The rollable sun cap according to claim 3, wherein the hair band portion (20) further comprises a pocket (26) formed on one side end thereof and a binding string (27) mounted on the open portion of the pocket (26) in such a manner as to bind the rolled up sun cap (1).

7. The rollable sun cap according to claim 2, wherein the hair band portion (20) comprises an outer skin (23) and a hair band core material (21) inserted into the outer skin (23).

* * * * *